United States Patent [19]

Brown et al.

[11] Patent Number: 4,507,300

[45] Date of Patent: Mar. 26, 1985

[54] PYRIDOTRIAZOLOPYRAZINE-DIONES FOR TREATING ALLERGY

[75] Inventors: Richard E. Brown, East Hanover, N.J.; Vassil St. Georgiev, New Rochelle, N.Y.; Philip Kropp, Meriden, Conn.; Bernard Loev, Scarsdale, N.Y.

[73] Assignee: USV Pharmaceutical Corporation, Tarrytown, N.Y.

[21] Appl. No.: 553,915

[22] Filed: Jun. 6, 1983

Related U.S. Application Data

[60] Division of Ser. No. 244,361, Mar. 16, 1981, Pat. No. 4,400,382, which is a continuation-in-part of Ser. No. 148,314, May 9, 1980, abandoned.

[51] Int. Cl.$^3$ ............... A61K 31/495; C07D 487/14; C07D 471/14; C07D 487/04
[52] U.S. Cl. .................................. 514/280; 544/350
[58] Field of Search ................... 544/350; 424/250

[56] References Cited

U.S. PATENT DOCUMENTS 4,008,322  2/1977  Dreikorn et al. ............... 424/250
4,354,027 10/1982  Loev et al. ..................... 544/346

OTHER PUBLICATIONS

Brown et al., Chem. Abs. 96, 69038t (1981).

*Primary Examiner*—Mark L. Berch

[57] ABSTRACT

New triazoloquinoxalin-1,4-diones are described as well as the use thereof as anti-allergenic agents.

5 Claims, No Drawings

PYRIDOTRIAZOLOPYRAZINE-DIONES FOR TREATING ALLERGY

This application is a division of previous application Ser. No. 244,361, filed Mar. 16, 1981, now U.S. Pat. No. 4,400,382, which was a continuation-in-part of application Ser. No. 148,314, filed May 9, 1980, now abandoned.

This invention relates to new anti-allergic agents and more particularly to certain new triazoloquinoxalin-1,4-diones possessing useful anti-allergic activity of particular use in the treatment of asthma.

The triazoloquinoxalin-1,4-diones of this invention are new compounds not previously described in the literature and show significant anti-allergy activity as shown in standard tests used for evaluation of such activity. These compounds show particularly significant activity in inhibiting formation of a wheal when screened according to the Rat Passive Cutaneous Anaphylaxis Screen [I. Mota, Life Science, 7, 465 (1963) and Z. Ovary, et al., Proceedings of Society of Experimental Biology and Medicine, 81, 584 (1952)]. The present new compounds also demonstrate potent activity as inhibitors of histamine release from passively sensitized Rat Mast cells according to the procedure described by E. Kusner, et al., Journal of Pharmacology and Therapeutics. Thus, the present new compounds are especially useful in the treatment of asthma and other allergic reactions.

The new compounds of this invention are of the following formulae:

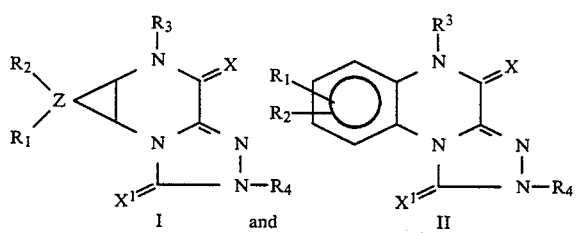

wherein,

X and $X^1$ are S or O and may be the same or different each of $R_1$ and $R_2$ is hydrogen, alkyl, alkenyl, alkynyl, cycloalkyl, aryl, aralkyl, sulfonamido, halogen, alkoxy, alkenyloxy, alkynyloxy, cyano, hydroxy, acyloxy, nitro, amino, alkylamino, alkanoylamino, carbalkoxyamino, methanesulfonyl, carboxy, carbalkoxy, trihalomethyl, or taken together, methylenedioxy;

each of $R_3$ and $R_4$ is hydrogen, alkyl, alkenyl, alkynyl, aryl, acyl, aralkyl, cycloalkyl, cycloalkyl, $CH_2$—, or carbalkoxy; and Z forms a heterocyclic ring with the two carbon atoms to which it is attached; and acid addition salts thereof, and where $R_4$ is hydrogen, the alkali and alkaline-earth metal salts thereof.

The total number of carbon atoms in each of such hydrocarbyl substituent can range up to about 10.

The preferred compounds are those in which the hydrocarbyl radicals contain up to about 7 carbon atoms when aliphatic and up to 10 carbon atoms when aromatic, e.g., phenyl, tolyl and naphthyl.

The heterocyclic ring of which Z is representative includes any 5 or 6-membered heterocyclic ring. Exemplary ring systems are those containing at least one hetero atom such as nitrogen, oxygen or sulfur and include thiophene, furan, pyrrole, pyran, pyridine, piperidine, pyrimidine, thiazole, oxazole, isothiazole and the like, as well as benzoheterocyclics such as benzofuran, benzothiophene, quinoline, isoquinoline and benzoxazole.

The particularly preferred compounds of the invention are those in which X is oxygen, that is the triazoloquinoxalin-1,4-diones.

The new compounds of the invention can be prepared by art-recognized procedures from known starting compounds. For example, the following procedure can be employed for compounds of formula I.

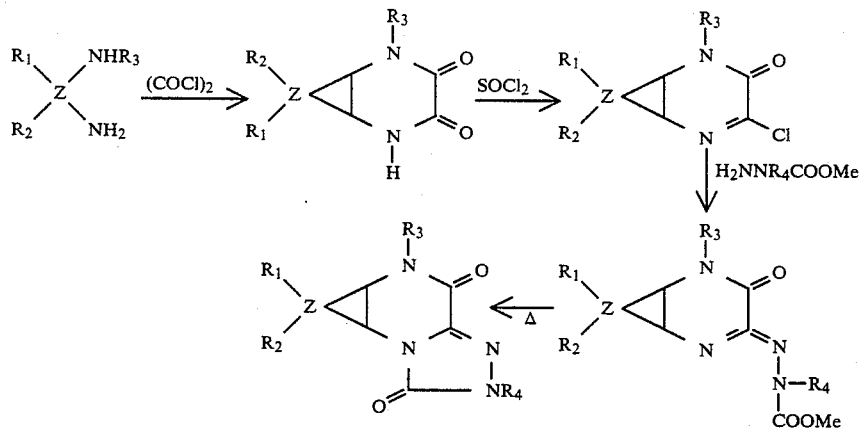

The sulfur analogs and compounds of Formula II can be prepared by analogous procedures.

Substituents $R_1$ to $R_4$ can be added after formation of the basic ring structures by known substitution reactions, or by conversion of substituents such as reduction of nitro to form amino. The substitution reactions mentioned include, for example, alkylation and acylation by known procedures.

Substituents on the present new compounds which are reactive and could interfere with ring closure reactions are best introduced by subsequent reactions known to the art such as reduction of nitro to amino, or hydrolysis of cyano to carboxamide or carboxy groups; alternatively, such reactive groups can be protected as by, for example, acylation of an amino group, followed by hydrolysis after ring closure.

Using the procedures described, a wide variety of heterocyclic compounds can be prepared, as follows:

$$\begin{array}{c} R_3 \\ | \\ R_2 \diagdown \phantom{Z} N \diagup X \\ \phantom{R_2}Z \diagup\!\!\!\diagdown \\ R_1 \diagup \phantom{Z} N \diagdown N \\ \phantom{XXXXX} | \\ X \diagup\!\!\!\diagdown\!\!\!\!\diagdown N - R_4 \end{array}$$

| $R_1$ | $R_2$ | Z | X and $X^1$ | $R_3$ | $R_4$ |
|---|---|---|---|---|---|
| H | H | furano | O | $CH_3$ | $COCH_3$ |
| $CH_3$ | H | thieno | O | $C_2H_5$ | n-$C_3H_7$ |
| $CH_3$ | $CH_3$ | thieno | O | $CH_3$ | i-$C_3H_7$ |
| Cl | H | pyrido | S | H | $C_6H_5$ |
| $OCH_3$ | H | pyrimido | O | $C_7H_{15}$ | $C_6H_5CH_2$— |
| $C_6H_5$ | H | pyrido | O | $C_6H_{11}$ | $CH_3C_6H_4$ |
| $CF_3$ | $CH_3$ | furano | O | $C_3H_7$ | $C_3H_7CO$ |
| $OC_3H_5$ | H | thieno | S | $C_6H_5CH_2$ | $COOCH_3$ |
| $OC_6H_5$ | H | thieno | O | $C_6H_5$ | $C_4H_9CO$ |
| H | H | pyrido | O | $C_{10}H_7$ | H |
| OH | $CH_3$ | piperidino | O | $C_3H_3$ | H |
| $C_4H_9$ | OH | benzo-furano | O | $C_6H_5CO$ | H |
| $CH_2OH$ | H | benzo-thieno | O | H | $C_4H_7$ |
| $NH_2$ | $OCH_3$ | quinolino | O | H | $C_4H_9$ |
| $NHCH_3$ | H | thieno | O | $CH_3$ | H |
| SH | H | thiazolino | O | $C_3H_7$ | H |
| $SC_3H_7$ | H | thiazolino | O | $C_2H_5$ | H |
| $C_4H_7$ | $OCH_3$ | thieno | O | $C_7H_{15}$ | H |
| $NO_2$ | H | furano | O | $CH_3$ | $CH_3CO$ |
| $C_6H_5CH_2O$ | H | thieno | O | H | $CH_3$ |
| $OCF_3$ | H | pyrido | O | H | $CH_3CO$ |
| $C_2H_4NH_2$ | H | pyrido | O | H | H |
| H | H | pyrido | O | $CH_3$ | H |
| H | H | pyrido | O | $CH_3$ | H |
| H | H | pyrido | O | $CH_3$ | H |

The present new heterocyclic compounds are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, succinic, arylsulfonic, e.g., p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystalization of the hydrochloride salt formed. The perchloric acid salts are useful for purification and crystallization of the new products.

Where $R_4$ is hydrogen, the alkali and alkaline-earth metal salts are of particular value because of their solubility. Any pharmaceutically-acceptable metal such as sodium, potassium, lithium, calcium, magnesium and the like may be used. The salts are readily obtained by treating the desired compound wherein $R_4$ is hydrogen with a suitable metal hydroxide or metal carbonate.

As therapeutic agents, the novel heterocyclic compounds of this invention are particularly useful as antiallergy agents acting via inhibition of mediator release. These compounds are active orally in the passive cutaneous anaphylaxis (PCA) screen; and/or inhibit histamine release from passively sensitized rat mast cells.

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-allergy agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The intermediate carbazate compounds which, on ring closure, form the new therapeutic agents of this invention are new compounds which are represented by the formulae:

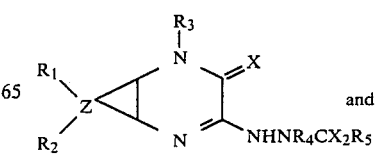

and

-continued

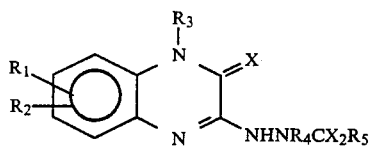

wherein $R_1$, $R_2$, $R_3$, $R_4$, Z and X are as hereinbefore described and $R_5$ is alkyl, preferably lower alkyl.

The new carbazate intermediates of the invention are prepared by art-recognized procedures as described herein. The intermediates also possess anti-allergic activity.

The following examples further illustrate the invention.

EXAMPLE 1

4-Methyl-(1H)pyrido(2,3-b)pyrazine-2,3-dione

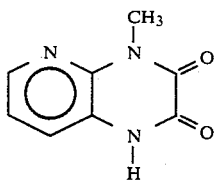

To a mixture of 8 ml. of oxalyl chloride in 150 ml. dichlorobenzene at 60° C. was added lowly 7.5 g. of 2-amino-3-methylaminopyridine. After completion of addition, the temperature of the reaction mixture was allowed to rise to 130° C. It was stirred at this temperature for 1 hour, filtered hot, and the solid washed with ether, m.p. 168°–174° C.

EXAMPLE 2

2-Chloro-4-methyl-pyrido(2,3-b)pyrazine-3-one

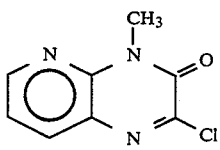

To a mixture of 5 ml. of thionyl chloride in 200 ml. of toluene and 5 ml. dimethylformamide at 70° C. was added 8.6 g. of 4-methyl(1H)-pyrido(2,3-b)pyrazine,2,3-dione. After addition, the reaction temperature was allowed to rise to 130° C. Stirring continued at this temperature for 2 hours.

The reaction mixture was then filtered hot, the filtrate evaporated to dryness, and the residue diluted with mixture of 1:1 ether-hexane and filtered to give 2-chloro-4-methyl-pyrido(2,3-b)pyrazine-3-one.

EXAMPLE 3

5-Methyl-pyrido(2,3-e)(1,2,4)triazolo(4,3-a)pyrazine-1,4-(2H,5H)dione

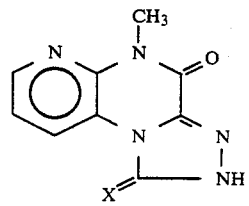

A mixture of 7.5 g. of 2-chloro-4-methyl-pyrido(2,3-b)pyrazine-3-one, and 4 g. of methyl carbazate in 200 ml. of Dowtherm A was stirred and heated at 80° C. for 1 hour and then at 230° C. for 20 minutes.

It was then cooled and filtered. The crude product was crystallized twice from acetic acid—$H_2O$ to give the title compound in pure form, m.p. >300° C.

EXAMPLE 4

2-Acetyl-5-methyl-pyrido(2,3-e)(1,2,4)triazolo(4,3-a)pyrazine-1,4-(2H,5H)dione

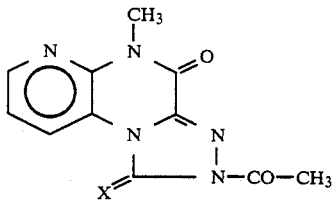

A mixture of 1.8 g. of 5-methyl-pyrido(2,3-e)(1,2.4)triazolo(4,3-a)pyrazine-1,4-(2H,5H)dione in 25 ml. of acetic anhydride and 50 ml. of acetic acid was stirred and refluxed for 5 hours.

The mixture was cooled, filtered, and the product was washed with water, dried and crystallized from acetic acid-ether, m.p. 298°–300° C.

EXAMPLE 5

5-Methyl-thieno(2,3-e)(1,2,4)triazolo(4,3-a)pyrazine-1,4-(2H,5H)dione

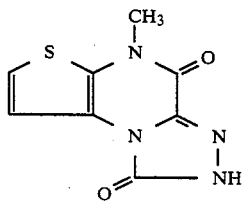

In the same way as described in Examples 1–3, 2-methylamino-3-aminothiophene was converted to the title compound.

EXAMPLE 6

5-Methyl-furo(2,3-e)(1,2,4)triazolo(4,3-a)pyrazine-1,4-(2H,5H)dione

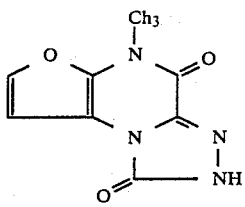

In the same way as described in Examples 1–3, 2-methylamino-3-aminofuran was converted to the title compound.

EXAMPLE 7

5-Methyl-1,2,4-triazolo(3',4':6,1)pyrazino(3,2-b)quinoline-1,4-(2H,5H)dione

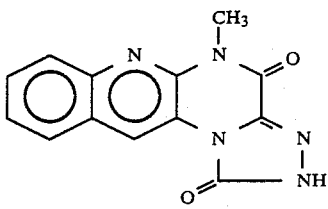

In the same way as described in Examples 1–3, 2-methylamino-3-aminoquinoline was converted to the title compound.

EXAMPLE 8

5-Methyl-1,2,4-triazolo(3',4':6,1)pyrazino(3,2-c)isoquinoline-1,4-(2H,5H)dione

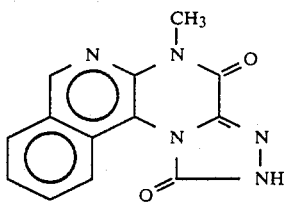

In the same way as described in Examples 1–3, 3-methylamino-4-aminoisoquinoline was converted to the title compound.

EXAMPLE 9

A. 1-Methylquinoxaline-2,3-dione

To a solution of 31 g. (0.36 m.) of oxalychloride in 50 ml. o-dichlorobenzene at 60° is added dropwise with stirring a solution of 31.3 g. (0.256 m.) N-methyl-o-phenylenediamine in 150 ml. of o-dichlorobenzene. The mixture is then heated over 1 hour to 160° C. and cooled to 20° C. The precipitated product is filtered, washed and dried, yield 82%, m.p. 277°–286° C. It may be purified by recrystallization from methanol, m.p. 286°–289° C.

B. 3-Chloro-1-methyl-1H-quinoxalin-2-one

A mixture of 56.1 g. (0.32 m.) of 1,4-dihydro-1-methylquinoxalin-2,3-dione, 10 ml. of DMF, 50 ml. (0.67 m.) of thionyl chloride and 1 l. of toluene was refluxed for 1 hour, cooled, and stripped, finally under high vacuum to a crude dark solid, m.p. 124°–130° C. of sufficient purity to use in the next step.

C. Ethyl-3-(1-methyl-2-oxo(2H)quinoxalin-3-yl)carbazate

A solution of 152 g. (0.78 m.) of 3-chloro-1-methyl-1H-quinoxalin-2-one, 116 g. (1.1 m.) of ethyl carbazate and 1 l. of acetonitrile is refluxed for 16 hours. The mixture is cooled to 9° C. and the product collected by filtration and used directly for cyclization.

In the same manner, the following carbazate compounds are obtained:
Ethyl-3-(2-oxo(2H)quinoxalin-3-yl)carbazate
Ethyl-3-(1-phenyl-2-oxo(2H)quinoxalin-3-yl)carbazate
Ethyl-3-(1,6-dimethyl-2-ono(2H)quinoxalin-3-yl)carbazate
Ethyl-3-(1,7-dimethyl-2-oxo(2H)quinoxalin-3-yl)carbazate
Ethyl-3-(1,8-dimethyl-2-oxo(2H)quinoxalin-3-yl)carbazate
Ethyl-3-(1-methyl-6-methoxy-2-oxo(2H)quinoxalin-3-yl)carbazate
Ethyl-3-(1-methyl-6-trifluoromethyl-2-oxo(2H)quinoxalin-3-yl)carbazate
Ethyl-3-(1-methyl-6,7-dimethoxy-2-oxo(2H)quinoxalin-3-yl)carbazate
Ethyl-3-(1-methyl-8-chloro-2-oxo(2H)quinoxalin-3-yl)carbazate
Ethyl-3-(1-methyl-6-carbomethoxy-2-oxo(2H)quinoxalin-3-yl)carbazate D. 1-Oxo-5-methyl-1H,4H(1,2,4)triazolo(4,3-a)quinoxalin-4-one 100 g of the product of Paragraph C is heated under nitrogen with constant stirring to 200°–260° C. for 30 minutes. After cooling, the yellow solid is finely powdered and extracted with 2 l. of hot acetonitrile. The insoluble material, m.p. 300° C., is analytically pure, but can be recrystallized from dimethysulfoxide.

In the same manner, the following products are obtained:
1-Oxo-1H,4H(1,2,4)triazolo(4,3-a)quinoxalin-4-one
1-Oxo-5-phenyl-1H,4H(1,2,4)triazolo(4,3-a)quinoxalin-4-one
1-Oxo-5,8-dimethyl-1H,4H(1,2,4)triazolo(4,3-a)quinoxalin-4-one
1-Oxo-5,7-dimethyl-1H,4H(1,2,4)triazolo(4,3-a)quinoxalin-4-one
1-Oxo-5,6-dimethyl-1H,4H(1,2,4)triazolo(4,3-a)quinoxalin-4-one
1-Oxo-5,7,8-trimethyl-1H,4H(1,2,4)triazolo(4,3-a)quinoxalin-4-one
1-Oxo-5-methyl-8-methoxy-1H,4H(1,2,4)triazolo(4,3-a)quinoxalin-4-one
1-Oxo-5-methyl-8-trifluoromethyl-1H,4H(1,2,4)triazolo(4,3-a)quinoxalin-4-one
1-Oxo-5-methyl-7,8-dimethoxy-1H,4H(1,2,4)triazolo(4,3-a)quinoxalin-4-one
1-Oxo-5-methyl-6-chloro-1H,4H(1,2,4)triazolo(4,3-a)quinoxalin-4-one
1-Oxo-5-methyl-8-carbomethoxy-1H,4H(1,2,4)triazolo(4,3-a)quinoline-4-one
1-Oxo-5-methyl-8-carboxy-1H,4H(1,2,4)triazolo(4,3-a)quinolin-4-one

EXAMPLE 10

1-Oxo-5-methyl-1H,4H(1,2,4)triazolo(4,3-a)quinoxalin-4-one 15 g. of the product of Paragraph C, Example 9 was added with stirring to Dowtherm A (200 ml.) at 230° C. The reaction mixture was kept at this temperature until cyclization was completed (usually less than 20 minutes at this or higher temperature).

Upon completion of cyclization, the reaction mixture was cooled, filtered, and the solid washed well with ethanol and methylene dichloride.

EXAMPLE 11

1-Oxo-2-acetyl-5-methyl-1H,4H(1,2,4)triazolo(4,3-a)quinoxalin-4-one

A mixture of 2.16 g. (0.01 mol) of the product of Paragraph D, Example 9, 30 ml. of pyridine and 30 ml. of acetic anhydride was refluxed for 1 hour, the solvent was evaporated and the residue recrystallized from acetonitrile, m.p. 288°–289° C.

EXAMPLE 12

Potassium-1-oxo-5-methyl-1H,4H(1,2,4)triazolo(4,3-a)quinoxaline-4-one-8-carboxylate A mixture of 2.0 g. of 1-oxo-5-methyl-8-carbomethoxy-1H,4H(1,2,4)triazolo(4,3-a)quinoxaline-4-one, 250 ml. of ethanol and 1 g. of potassium hydroxide was refluxed for 2 hours. The acid dissolved to give a clear solution, then a precipitate formed which was filtered, washed with alcohol and dried, m.p. 300° C.

EXAMPLE 13

1-Oxo-5-propyl-7-chloro-1H,4H(1,2,4)-triazolo(4,3a)-quinoxalin-4-one

A. 100 g ethyl-3-(1-propyl-7-chloro-2-oxo(2H-)quinoxalin-3yl)-carbazate was heated under nitrogen with constant stirring at 200°–260° C. for about 30 minutes. After cooling, the yellow solid product was finely powderd and extracted with hot acetonitrile to remove colored impurities. The residue was analytically pure with an m.p. 281°–3° C.

B. Preparation of sodium salt.

35 g of 1-oxo-5-propyl-1H,4H(1,2,4)-triazolo(4,3-a)quinoxaline-4-one, 50 ml methanol, 400 ml water and 140 ml 1N NaOH were heated to about 90° C. and heating was continued until complete solution occurred. On cooling the sodium salt crystallized. The solid sodium salt was filtered, washed first with water and then with acetone and dried in vacuo at about 50° C. m.p. 356°–7° C.

Following the procedure described in B. above, the corresponding salts of potassium, m.p. 335°–50° C., and lithium, m.p. 305°–8° C., were obtained as their monhydrates.

Other compounds of formula II wherein both X and $X^1$ are O and prepared by the procedure in example 13A include:

| $R_1$ | $R_2$ | $R_3$ | m.p. °6 |
|---|---|---|---|
| H | H | n-Pr | 235-6 |
| 7-Cl | H | Me | 300 |

The compounds of this invention are useful antiallergic agents. Exemplary of the present new compounds is 6-methylpyrido(2,3-e) (1,2,4)triazolo(4,3-a)pyrazine-1,4-(2H,4H)dione which reduced wheal formation by 53% at 25 mg./kg. (p.o.) when screened according to the Rat Passive Cutaneous Anaphylaxis Screen as described by I. Mota, Life Sciences, 7, 465 (1963) and Z. Ovary, et al., Proceedings of Society of Experimental Biology and Medicine, 81, 584 (1952). In addition, the said compound showed an $I_{50}$ of 9.0 μM in inhibition of histamine release from passively sensitized rat mast cells according to the procedure described by E. Kusner, et al., Journal of Pharmacology and Experimental Therapeutics.

What is claimed is:

1. An anti-allergic compound of the formula:

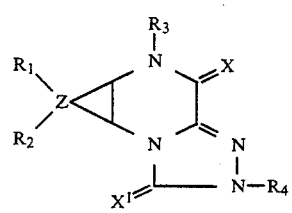

wherein, $X$ and $X^1$ are S or O and may be the same or different;

each of $R_1$ and $R_2$ is hydrogen, $C_1$–$C_{10}$ alkyl, $C_2$–$C_{10}$ alkenyl, $C_2$–$C_{10}$ alkynyl, $C_3$–$C_{10}$ cycloalkyl, $C_6$–$C_{10}$ aryl, $C_6$–$C_{10}$-ar-$C_1$–$C_{10}$-alkyl, sulfonamido, halogen, $C_1$–$C_{10}$ alkoxy, $C_2$–$C_{10}$ alkenyloxy, $C_2$–$C_{10}$ alkynyloxy, cyano, hydroxy, nitro, amino, $C_1$–$C_{10}$ alkylamino, $C_1$–$C_{10}$ alkanoylamino, carb-$C_1$–$C_{10}$-alkoxyamino, methanesulfonyl, carboxy, carb-$C_1$–$C_{10}$-alkoxy, trihalomethyl, or taken together, methylenedioxy;

each of $R_3$ and $R_4$ is hydrogen, $C_1$–$C_{10}$ alkyl, $C_2$–$C_{10}$ alkenyl, $C_2$–$C_{10}$ alkynyl, $C_6$–$C_{10}$ aryl, $C_1$–$C_{10}$ alkanoyl, benzoyl, $C_6$–$C_{10}$-ar-$C_1$–$C_{10}$-alkyl, $C_3$–$C_{10}$ cycloalkyl, $C_3$–$C_{10}$-cycloalkyl $CH_2$—, or carb-$C_1$–$C_{10}$-alkoxy; and $Z$ forms a pyridyl ring with the two carbon atoms to which it is attached; and pharmaceutically acceptable acid additon salts thereof, and where $R_4$ is hydrogen, the pharmaceutically acceptable alkali and alkaline-earth metal salts thereof.

2. An anti-allergic compound of the formula

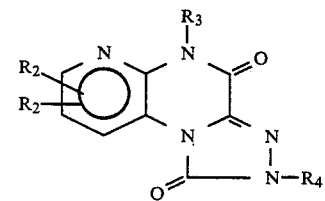

wherein, each of $R_1$ and $R_2$ is hydrogen, $C_1$–$C_{10}$ alkyl, $C_2$–$C_{10}$ alkenyl, $C_2$–$C_{10}$ alkynyl, $C_3$–$C_{10}$ cycloalkyl, $C_6$–$C_{10}$ aryl, $C_6$–$C_{10}$-ar-$C_1$–$C_{10}$-alkyl, sulfonamido, halogen, $C_1$–$C_{10}$ alkenyloxy, $C_2$–$C_{10}$ alkynyloxy, cyano, hydroxy, nitro, amino, $C_1$–$C_{10}$ alkylamino, $C_1$–$C_{10}$ alkanoylamino, carb-$C_1C_{10}$-alkoxyamino, methanesulfonyl, carboxy, carb-$C_1$–$C_{10}$-alkoxy, trihalomethyl, or taken together, methylenedioxy;

each of $R_3$ and $R_4$ is hydrogen, $C_1$–$C_{10}$ alkyl, $C_2$–$C_{10}$ alkenyl, $C_2$–$C_{10}$ alkynyl, $C_6$–$C_{10}$ aryl, $C_1$–$C_{10}$ alkanoyl, benzoyl, $C_6$–$C_{10}$-ar-$C_1$–$C_{10}$-alkyl, $C_3$–$C_{10}$ cycloalkyl, $C_3$–$C_{10}$-cycloalkyl $CH_2$—, or carb-$C_1$–$C_{10}$-alkoxy;

pharmaceutically acceptable acid addition salts thereof; and where $R_4$ is hydrogen, the pharmaceutically acceptable alkali and alkaline-earth metal salts thereof.

3. 5-Methyl-pyrido[2,3-e]-[1,2,4]-triazolo-[4,3-a]-pyrazine-1,4-[2H,5H]-dione.

4. 2-Acetyl-5-methyl-pyrido[2,3-e]-[1,2,4]-triazolo-[4,3-a]-pyrazine-1,4-[2H,5H]-dione.

5. A pharmaceutical composition containing a compound according to claim 1 in an amount effective as an antiallergic agent and a pharmaceutically acceptable carrier.

* * * * *